(12) United States Patent
Batycky et al.

(10) Patent No.: US 7,384,649 B2
(45) Date of Patent: *Jun. 10, 2008

(54) PARTICULATE COMPOSITIONS FOR PULMONARY DELIVERY

(75) Inventors: Richard P. Batycky, Newton, MA (US); David A. Edwards, Boston, MA (US); Michael M. Lipp, Framingham, MA (US)

(73) Assignee: Advanced Inhalation Research, Inc., Cambridge, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/633,750

(22) Filed: Dec. 5, 2006

(65) Prior Publication Data

US 2007/0104657 A1 May 10, 2007

Related U.S. Application Data

(63) Continuation of application No. 10/300,657, filed on Nov. 20, 2002, now Pat. No. 7,182,961.

(60) Provisional application No. 60/331,708, filed on Nov. 20, 2001.

(51) Int. Cl.
*A61K 9/50* (2006.01)

(52) U.S. Cl. .................................... 424/428

(58) Field of Classification Search ............... 424/489, 424/490, 491, 493, 499, 498, 46
See application file for complete search history.

(56) References Cited

U.S. PATENT DOCUMENTS

| 2,470,296 | A | 5/1949 | Fields |
| 2,533,065 | A | 12/1950 | Taplin et al. |
| 2,992,645 | A | 7/1961 | Fowler |
| 3,781,230 | A | 12/1973 | Vassiliades et al. |
| 3,957,965 | A | 5/1976 | Harley et al. |

(Continued)

FOREIGN PATENT DOCUMENTS

CA 2085884 12/1991

(Continued)

OTHER PUBLICATIONS

Abdellaziz Ben-Jebria et al., "Large Porous Particles for Sustained Protection from Carbachol-Induced Bronchoconstriction in Guinea Pigs," *Pharmaceutical Research*, 16:4 (1999).

(Continued)

*Primary Examiner*—Sharon E. Kennedy
(74) *Attorney, Agent, or Firm*—Elmore Patent Law Group; Carolyn S. Elmore; Darlene A. Vanstone (57) ABSTRACT

This invention concerns an improved particulate composition for delivering a drug to the pulmonary system. Applicants disclose a method of identifying an optimal form of aerodynamically light particles which are highly dispersible. The particles of the instant invention are made by creating hollow, spherical drug particles (i.e., progenitor particles) that collapse in the process of particle formation, leading to wrinkled, thin-walled drug particles of very low envelope density. Additionally, Applicants have found that such particles are especially optimal for inhaled aerosols when the surface area parameter ($\sigma$) is greater than 2, optimally greater than 3.

17 Claims, 5 Drawing Sheets

U.S. PATENT DOCUMENTS

| | | |
|---|---|---|
| 4,009,280 A | 2/1977 | Macarthur et al. |
| 4,089,800 A | 5/1978 | Temple |
| 4,161,516 A | 7/1979 | Bell |
| 4,173,488 A | 11/1979 | Vassiliades et al. |
| 4,272,398 A | 6/1981 | Jaffe |
| 4,352,883 A | 10/1982 | Lim |
| 4,391,909 A | 7/1983 | Lim |
| 4,466,442 A | 8/1984 | Hilmann et al. |
| 4,480,041 A | 10/1984 | Myles et al. |
| 4,524,769 A | 6/1985 | Wetterlin |
| 4,572,203 A | 2/1986 | Feinstein |
| 4,590,206 A | 5/1986 | Forrester et al. |
| 4,615,697 A | 10/1986 | Robinson |
| 4,679,555 A | 7/1987 | Sackner |
| 4,741,872 A | 5/1988 | De Luca et al. |
| 4,743,545 A | 5/1988 | Torobin |
| 4,774,958 A | 10/1988 | Feinstein |
| 4,789,550 A | 12/1988 | Hommel et al. |
| 4,818,542 A | 4/1989 | De Luca et al. |
| 4,847,091 A | 7/1989 | Illum |
| 4,855,144 A | 8/1989 | Leong et al. |
| 4,857,311 A | 8/1989 | Domb et al. |
| 4,861,627 A | 8/1989 | Mathiowitz et al. |
| 4,865,789 A | 9/1989 | Castro et al. |
| 4,895,719 A | 1/1990 | Radakrishnan et al. |
| 4,904,479 A | 2/1990 | Illum |
| 4,917,119 A | 4/1990 | Potter et al. |
| 4,963,297 A | 10/1990 | Madden |
| 4,976,968 A | 12/1990 | Steiner |
| 4,994,281 A | 2/1991 | Muranishi et al. |
| 4,995,385 A | 2/1991 | Valentini et al. |
| 5,033,463 A | 7/1991 | Cocozza |
| 5,064,650 A | 11/1991 | Lew |
| 5,069,936 A | 12/1991 | Yen |
| 5,075,109 A | 12/1991 | Tice et al. |
| 5,100,669 A | 3/1992 | Hyon et al. |
| 5,123,414 A | 6/1992 | Unger |
| 5,145,684 A | 9/1992 | Liversidge et al. |
| 5,160,745 A | 11/1992 | De Luca et al. |
| 5,169,871 A | 12/1992 | Hughes et al. |
| 5,174,988 A | 12/1992 | Mautone et al. |
| 5,195,520 A | 3/1993 | Schlief et al. |
| 5,204,108 A | 4/1993 | Illum |
| 5,204,113 A | 4/1993 | Hartley et al. |
| 5,260,306 A | 11/1993 | Boardman et al. |
| 5,271,961 A | 12/1993 | Mathiowitz et al. |
| 5,306,483 A | 4/1994 | Mautone |
| 5,327,883 A | 7/1994 | Williams et al. |
| 5,334,381 A | 8/1994 | Unger |
| 5,340,587 A | 8/1994 | Milhalko et al. |
| 5,352,435 A | 10/1994 | Unger |
| 5,384,133 A | 1/1995 | Boyes et al. |
| 5,393,524 A | 2/1995 | Quay |
| 5,407,609 A | 4/1995 | Tice et al. |
| 5,456,917 A | 10/1995 | Wise et al. |
| 5,466,841 A | 11/1995 | Horrobin et al. |
| 5,482,946 A | 1/1996 | Clark et al. |
| 5,518,709 A | 5/1996 | Sutton et al. |
| 5,518,998 A | 5/1996 | Bäckström et al. |
| 5,551,489 A | 9/1996 | Trofast et al. |
| 5,580,575 A | 12/1996 | Unger et al. |
| 5,607,695 A | 3/1997 | Ek et al. |
| 5,607,915 A | 3/1997 | Patton |
| 5,612,053 A | 3/1997 | Baichwal et al. |
| 5,614,216 A | 3/1997 | Janoff |
| 5,654,007 A | 8/1997 | Johnson |
| 5,690,954 A | 11/1997 | Illum |
| 5,698,721 A | 12/1997 | Heath |
| 5,707,644 A | 1/1998 | Illum |
| 5,709,884 A | 1/1998 | Trofast et al. |
| 5,780,014 A | 7/1998 | Eljamal |
| 5,795,594 A | 8/1998 | York et al. |
| 5,804,212 A | 9/1998 | Illum |
| 5,814,607 A | 9/1998 | Patton |
| 5,830,853 A | 11/1998 | Bäckström et al. |
| 5,851,453 A | 12/1998 | Hanna et al. |
| 5,855,913 A | 1/1999 | Hanes et al. |
| 5,874,063 A | 2/1999 | Briggner et al. |
| 5,874,064 A | 2/1999 | Edwards et al. |
| 5,885,613 A | 3/1999 | Holland et al. |
| 5,902,802 A | 5/1999 | Heath |
| 5,922,354 A | 7/1999 | Johnson |
| 5,928,469 A | 7/1999 | Franks et al. |
| 5,976,574 A | 11/1999 | Gordon |
| 5,985,248 A | 11/1999 | Gordon |
| 5,985,309 A | 11/1999 | Edwards et al. |
| 5,993,783 A | 11/1999 | Eljamal |
| 5,994,314 A | 11/1999 | Eljamal et al. |
| 5,997,848 A | 12/1999 | Patton et al. |
| 6,001,336 A | 12/1999 | Gordon |
| 6,019,968 A | 2/2000 | Platz |
| 6,045,828 A | 4/2000 | Bystrom et al. |
| 6,051,256 A | 4/2000 | Platz |
| 6,063,138 A | 5/2000 | Hanna et al. |
| 6,077,543 A | 6/2000 | Gordon et al. |
| 6,080,721 A | 6/2000 | Patton |
| 6,080,762 A | 6/2000 | Allen et al. |
| 6,103,270 A | 8/2000 | Johnson |
| 6,123,936 A | 9/2000 | Platz |
| 6,136,295 A | 10/2000 | Edwards et al. |
| 6,136,346 A | 10/2000 | Eljamal |
| 6,153,224 A | 11/2000 | Staniforth |
| RE37,053 E | 2/2001 | Hanes et al. |
| 6,187,330 B1 | 2/2001 | Wang et al. |
| 6,187,344 B1 | 2/2001 | Eljamal et al. |
| 6,231,851 B1 | 5/2001 | Platz et al. |
| 6,258,341 B1 | 7/2001 | Foster |
| 6,284,282 B1 | 9/2001 | Maa et al. |
| 6,284,283 B1 | 9/2001 | Costantino et al. |
| 6,303,582 B1 | 10/2001 | Eljamal |
| 6,309,623 B1 | 10/2001 | Weers et al. |
| 6,309,671 B1 | 10/2001 | Foster |
| 6,315,983 B1 | 11/2001 | Eistetter |
| 6,358,530 B1 | 3/2002 | Eljamal |
| 6,395,300 B1 | 5/2002 | Straub et al. |
| 6,426,210 B1 | 7/2002 | Franks et al. |
| 6,433,040 B1 | 8/2002 | Dellamary et al. |
| 6,521,260 B1 | 2/2003 | Staniforth |
| 2002/0052310 A1 | 5/2002 | Edwards et al. |

FOREIGN PATENT DOCUMENTS

| | | |
|---|---|---|
| CA | 1300009 | 5/1992 |
| CA | 1302258 | 6/1992 |
| CA | 2166108 | 1/1995 |
| CA | 2170394 | 2/1995 |
| CA | 2111002 | 8/2000 |
| CA | 2058428 | 9/2000 |
| CA | 2126244 | 9/2000 |
| EP | 0 257 915 A1 | 3/1988 |
| EP | 0 324 938 A1 | 7/1989 |
| EP | 0 335 133 A2 | 10/1989 |
| EP | 0 458 745 A1 | 5/1991 |
| EP | 0 213 303 B1 | 9/1991 |
| EP | 0 257 956 B1 | 5/1992 |
| EP | 0 510 731 A1 | 10/1992 |
| EP | 0 634 166 A1 | 1/1995 |
| EP | 0 656 206 A1 | 6/1995 |
| EP | 0 072 046 A1 | 2/2003 |
| GB | 1 288 583 | 11/1969 |
| WO | WO 80/02365 | 11/1980 |
| WO | WO 86/06959 | 12/1986 |
| WO | WO 88/09163 | 1/1988 |
| WO | WO 88/04556 | 6/1988 |

| | | |
|---|---|---|
| WO | WO 91/04732 | 4/1991 |
| WO | WO 91/06286 | 5/1991 |
| WO | WO 91/06287 | 5/1991 |
| WO | WO 91/12823 | 9/1991 |
| WO | WO 91/16882 | 11/1991 |
| WO | WO 92/18164 | 10/1992 |
| WO | WO 92/21382 | 12/1992 |
| WO | WO 93/25221 | 12/1993 |
| WO | WO 94/04133 | 3/1994 |
| WO | WO 94/07514 | 4/1994 |
| WO | WO 94/08627 | 4/1994 |
| WO | WO 94/16739 | 8/1994 |
| WO | WO 95/00127 | 1/1995 |
| WO | WO 95/07072 | 3/1995 |
| WO | WO 95/24183 | 9/1995 |
| WO | WO 95/31479 | 11/1995 |
| WO | WO 95/35097 | 12/1995 |
| WO | WO 96/09814 | 4/1996 |
| WO | WO 96/15814 | 5/1996 |
| WO | WO 96/23485 | 8/1996 |
| WO | WO 96/32096 | 10/1996 |
| WO | WO 96/32116 | 10/1996 |
| WO | WO 96/32149 | 10/1996 |
| WO | WO 96/40963 | 12/1996 |
| WO | WO 96/41873 | 12/1996 |
| WO | WO 97/03649 | 2/1997 |
| WO | WO 98/29096 | 7/1997 |
| WO | WO 98/29098 | 7/1997 |
| WO | WO 97/36574 | 10/1997 |
| WO | WO 97/41833 | 11/1997 |
| WO | WO 98/16205 | 4/1998 |
| WO | WO 98/29140 | 7/1998 |
| WO | WO 98/29141 | 7/1998 |
| WO | WO 98/31346 | 7/1998 |
| WO | WO 98/51278 | 11/1998 |
| WO | WO 99/16419 | 4/1999 |
| WO | WO 99/16420 | 4/1999 |
| WO | WO 99/16421 | 4/1999 |
| WO | WO 99/16422 | 4/1999 |
| WO | WO 99/66903 | 12/1999 |
| WO | WO 00/10541 | 3/2000 |
| WO | WO 00/15262 | 3/2000 |
| WO | WO 00/21594 | 4/2000 |
| WO | WO 00/33811 | 6/2000 |
| WO | WO 01/00312 A1 | 1/2001 |
| WO | WO 01/13891 A3 | 3/2001 |
| WO | WO 01/32144 A1 | 5/2001 |
| WO | WO 02/09669 A3 | 2/2002 |
| WO | WO 02/11695 A3 | 2/2002 |
| WO | WO 02/054868 A2 | 7/2002 |
| WO | WO 02/055101 A2 | 7/2002 |
| WO | WO 02/067902 | 9/2002 |
| WO | WO 02/085326 | 10/2002 |
| WO | WO 02/087542 A1 | 11/2002 |
| WO | WO 03/043586 | 5/2003 |

OTHER PUBLICATIONS

Adjei, A., and Garren, J., "Pulmonary Delivery of Peptide Drugs: Effect of Particle Size on Bioavailability of Leuprolide Acetate in Healthy Male Volunteers," *Pharm. Res.*, 7(6):565-569 (1990).

Allen, T.M., et al., "Subcutaneous Administration of Liposomes: A Comparison with the Intravenous and Intraperitoneal Routes of Injection," *Biochem. et Biophys. Acta.* 1150:9-16 (1993).

Altshuler, B., et al., "Aerosol Deposition in the Human Respiratory Tract," *Am. Med. Assoc. Arch. of Indust. Health* 15:293-303 (1957).

Anderson, P.J., et al., "Effect of Cystic Fibrosis on Inhaled Aerosol Boluses," *Am. Rev. Respir. Dis.*, 140:1317-1324 (1989).

Anderson, M., et al., "Human Deposition and Clearance of 6-μm Particles Inhaled with an Extremely Low Flow Rate," *Exp. Lung Res.* 21:187-195 (1995).

Barrera, D.A., et al., "Synthesis and RGD Peptide Modification of a New Biodegradable Copolymer: Poly(lactic acid-co-lysine)," *J. Am. Chem. Soc.*, 115:11010-11011 (1993).

Beck, L.R., et al., "A New Long-Acting Injectable Microcapsule System for the Administration of Progesterone," *Fertility and Sterility*, 31(5):545-551 (1979).

Benita, S., et al., "Characterization of Drug-loaded Poly(*d,l*-lactide) Microspheres," *J. of Pharm. Sci* 73(12):1721-1724 (1984).

Blackett, P.M., and G. Buckton, "A Microcalorimetric Investigation of the Interaction of Surfactants with Crystalline and Partially Crystalline Salbutamol Sulphate in a Model Inhalation Aerosol System," *Pharmaceutical Research*, 12(11):1689-1693 (1995).

Brian, J.D., "Physiology and Pathophysiology of Pulmonary Macrophages". In *The Reticuloendothelial System*, Reichard and Filkins, eds. (Plenum Press, New York), pp. 315-327 (1985).

Brown, A.R., et al., "Propellant-Driven Aerosols of Functional Proteins as Potential Therapeutic Agents in the Respiratory Tract," *Immunopharmacology*, 28:241-257 (1994).

Byron, P.R., "Determinants of Drug and Polypeptide Bioavailability from Aerosols Delivered to the Lung," *Adv. Drug. Del. Rev.*, 5:107-132 (1990).

Carroll, B.A., et al., "Gelatin Encapsulated Nitrogen Microbubbles as Ultrasonic Contrast Agents," *Investigative Radiology*, 15:260-266 (1980).

Carroll, B.A., et al., "Ultrasonic Contrast Enhancement of Tissue by Encapsulated Microbubbles," *Radiology*, 143:747-750 (1982).

Ch'ng, H.S., et al., "Bioadhesive Polymers as Platforms for Oral Controlled Drug Delivery II: Synthesis and Evaluation of Some Swelling, Water-Insoluble Bioadhesive Polymers," *J. of Pharm. Sci.*, 74(4):399-405 (1985).

Clark, A., and P. Byron, "Dependence of Pulmonary Absorption Kinetics on Aerosol Particle Size," *Z. Erkrank. Atm.org.*, 166:13-24 (1986).

Clark, A.R., and M. Egan, "Modeling the Deposition of Inhaled Powdered Drug Aerosols," *J. Aerosol Sci.*, 25(1):175-186 (1994).

Clay, M.M., et al. "Effect of Aerosol Particle Size on Bronchodilatation with Nebulised Terbutaline in Asthmatic Subjects," *Thorax* 41:364-368(1986).

Cohen, S., et al., "Controlled Delivery Systems for Proteins Based on Poly(Lactic/Glycolic Acid) Microspheres," *Pharm. Res.* 8(6):713-720(1991).

Colthorpe, P., et al., "The Pharmacokinetics of Pulmonary-Delivered Insulin: A Comparison of Intratracheal and Aerosol Administration to the Rabbit," *Pharm. Res.* 9(6):764-768 (1992).

Daly, W.H., et al., "The Preparation of N-Carboxyanhydrides of α-Amino Acids Using Bis(Trichloromethyl) Carbonate," *Tetrahedron Lett.*, 29(46):5859-5862 (1988).

Damms, B. and W. Bains, "The Cost of Delivering Drugs without Needles," *J. Controlled Release*, 8-11 (1996).

Darquenne, C., and M. Paiva, "Two and Three-Dimensional Simulations of Aerosol Transport and Deposition in Alveolar Zone of Human Lung," *Journal of Applied Physiology*, 80(4):1401-1414 (1996).

Davies, C.N., et al., "Breathing of Half-micron Aerosols. I. Experimental.," *J. of Appl. Physiol.* 32(5):591-600(1972).

David, S.S., and L. Illum, "Polymeric Microspheres as Drug Carriers," *Biomaterials*, 9:111-115 (1988).

David, S.S., et al., "Microspheres as Controlled-Release Systems for Parenteral and Nasal Administration," *Controlled Release Technology*, Chapter 15, pp. 201-213 (1987).

Dorries, A.M., and Valberg P.A., "Heterogeneity of Phagocytosis for Inhaled Versus Instilled Material," *Am. Rev. Respir. Dis.*, 146:831-837 (1992).

Edwards, D.A., "The Macrotransport of Aerosol Particles in the Lung: Aerosol Deposition Phenomena," *J. Aerosol Sci.*, 26(2):293-317 (1995).

Edwards, D.A., et al., "Large Porous Particles for Pulmonary Drug Delivery," *Science* 276:1868-71 (1997).

Eldridge, J. H., et al., "Biodegradable Microspheres as a Vaccine Delivery System," *Mol. Immunol.*, 28(3):287-294 (1991).

Feinstein, S.B., et al., "Two-Dimensional Contrast Echocardiography I. In Vitro Development and Quantitative Analysis of Echo Contrast Agents," *JACC* 3(1):14-20 (1984).

Ferin, J., et al., "Pulmonary Retention of Ultrafine and Fine Particles in Rats," *Am. J. Respir. Cell Mol. Biol.* 6:535-542 (1992).

Findeisen, W. "Uber Das Absetzen Kleiner, in Der Luft Suspendierter Teilchen in Der Menshlichen Lunge Bei Der Atmung," *Pflugers Arch. D. Ges. Physiol.* 236:367-379 (1935).

French, D.L, et al., "The Influence of Formulation on Emission, Deaggregation and Deposition of Dry Powders for Inhalation," *J. Aerosol Sci.*, 27(5):769-783 (1996).

Ganderton, D., "Generation of Respirable Clouds Form Coarse Powder Aggregates," *J. Biopharmaceutical Sciences*, 3(½):101-105 (1992).

Gehr, P. et al., "Surfactant and Inhaled Particles in the Conducting Airways: Structural, Stereological, and Biophysical Aspects," *Microscopy Res. And Tech.*, 26:423-436 (1993).

Gerrity, T.R., et al., "Calculated Deposition of Inhaled Particles in the Airways Generations of Normal Subject," *J. Appl. Phys.*, 47(4):867-873 (1979).

Gonda, I., "Aerosols for Delivery of Therapeutic and Diagnostic Agents to the Respiratory Tract," in *Critical Reviews in Therapeutic Drug Carrier Systems*, 6:273-313 (1990).

Gonda, I., "Preface. Major Issues and Future Prospects in the Delivery of Therapeutic and Diagnostic Agents to the Respiratory Tract," *Adv. Drug Del. Rev.* 5:1-9 (1990).

Gonda, I., "Physico-chemical Principles in Aerosol Delivery," in *Topics in Pharmaceutical Sciences* 1991, Crommelin, D.J. and K.K. Midha, Eds., Medpharm Scientific Publishers, Stuttgart, pp. 95-117 (1992).

Gonda, I., "Targeting by Desposition," in Pharmeceutical Inhalation Aersol Technology (ed. A.J. Hickey), Marcel Dekkar Inc., pp. 61-82, New York (1992).

Gurny, R., et al., "Bioadhesive Intraoral Release Systems: Design, Testing and Analysis," *Biomaterials*, 5: 336-340 (1984).

Hanes, J., et al., "Porous Dry-powder PLGA Microspheres Coated with Lung Surfactant for Systemic Insulin Delivery Via the Lung," *Proc. Int. Symp. Control. Rel. Bioact. Mater.*, 24:57-58 (1997).

Heyder, J., et al., "Deposition of Particles in the Human Respiratory Tract in the Size Range 0.005-15 µm," *J. Aerosol. Sci.*, 17(5):811-825 (1986).

Heyder, J., and G. Rudolf, "Mathematical models of particle deposition in the human respiratory tract," *J. Aerosol Sci.*, 15:697-707 (1984).

Heyder, J., et al., "Total Deposition of Aerosol Particles in the Human Respiratory Tract for Nose and Mouth Breathing," *J. Aerosol Sci.*, 6:311-328 (1975).

Hickey, A.J., et al., "Use of Particle Morphology to Influence the Delivery of Drugs from Dry Powder Aerosols," *J. Biopharmaceutical Sci.*, 3(½):107-113 (1992).

Hirano, S., et al., "Pulmonary Clearance and Toxicity of Zinc Oxide Instilled into the Rat Lung," *Arch. of Toxicology*, 63:336-342 (1989).

Hrkach, et al., "Synthesis of Poly(L-lactic acid-co-L-lysine) Graft Copolymers," *Macromolecules*, 28(13):4736-4739 (1995).

Hrkach, J.S., et al., "Poly(L-Lactic acid-co-amino acid) Graft Copolymers: A Class of Functional Biodegradable Biomaterials" in Hydrogels and Biodegradable Polymers for Bioapplications, ACS Symposium Series No. 627, Raphael M. Ottenbrite, et al., Eds., Americal Chemical Society, Chapter 8, pp. 93-101, 1996.

Illum, L., et al., "Bioadhesive Microspheres as a Potential Nasal Drug Delivery System,"*Int. J. of Pharm.* 39:189-199 (1987).

Johnson, M.A., et al., "Delivery of Albuterol and Ipratrophiumbromide from Two Nebulizer Systems in Chronic Stable Asthma: Efficacy and Pulmonary Deposition," *Chest*, 96:6-10 (1989).

Kao, Y.J., and R.L. Juliano, "Interactions of Liposomes with the Reticuloendothelial System, Effects of Reticuloendothelial Blockade on the Clearance of Large Unilamellar Vesicles," *Biochimica et Biophys. Acta.* 677:453-461 (1981).

Kassem, N.M., and D. Ganderton, "The Influence of Carrier Surface on the Characteristics of Inspirable Powder Aerosols," *J. Pharm. Pharmacol.*, 42(Supp):11 (1990).

Kawaguchi, H. et al., "Phagocytosis of Latex Particles by Leukocytes. I. Dependence of Phagocytosis on the Size and Surface Potential of Particles," *Biomaterials* 7:61-66 (1986).

Kobayashi, S. et al., "Pulmonary Delivery of Salmon Calcitonin Dry Powders Containing Absorption Enhancers in Rats," *Pharm. Res.*, 13(1):80-83 (1996).

Kohler, D., "Aerosols for Systemic Treatment" *Lung*, Suppl: pp. 677-684 (1990).

Komada, F. et al., Intratracheal Delivery of Peptide and Protein Agents: Absorption from Solution and Dry Powder by Rat Lung, *J. Pharm Sci.*, 83(6): 863-867 (Jun. 1994).

Krenis, L.J. and B. Strauss, "Effect of Size and Concentration of Latex Particles on Respiration of Human Blood Leucocytes," *Proc. Soc. Exp. Med.*, 107: 748-750 (1961).

Kricheldorf, H.R. "α-Aminoacid-N-Carboxy-Anhydrides and Related Heterocycles," Springer-Verlag, Berlin (1987).

Kwok, K.K., et al., "Production of 5-15 µm Diameter Alginate Polylysine Microcapsules by an Air Atomization Technique," Pharm. Res., 8(3):341-344 (1991).

Lai, Y-L., et al., "Sustained Bronchodilation with Isoproterenol Poly(Glycolide-co-Lactide) Microspheres," *Pharm. Res.*, 10(1):119-125 (1993).

Lai, W.C., et al., "Protection Against *Mycoplasma pulminosis* infection by Genetic Vaccination," *DNA and Cell Biology*,14(7):643-651 (1995).

Landahl, "On The Removal of Air-borne Droplets by The Human Respiratory Tract: I. The Lung," *Bull. Math. Biophys.*, 12:43-56 (1950).

Langer, R., "New Methods of Drug Delivery", *Science*, 249:1527-1533 (1990).

Le Corre, P., et al., "Preparation and Characterization of Bupivacaine-Loaded Polylactide and Polylactide-Co-Glycolide Microspheres," *Int. J. of Pharmaceutics*, 107:41-49 (1994).

Leone-Bay, A., et al., "Microsphere Formation in a Series of Derivatized α-Amino Acids: Properties, Molecular Modeling, and Oral Delivery of Salmon calcitonin," *J. of Med. Chem.*, 38(21):4257-4262 (1995).

Liu, F., et al., "Pulmonary Delivery of Free and Liposomal Insulin," *Pharm. Res.* 10(2):228-232 (1993).

Liu, W.R., et al., "Moisture-Induced Aggregation of Lyophilized Proteins in the Solid State," *Biotechnol. and Bioeng.*, 37:177-184 (1991).

Lo, Y. et al., "Protein Location in Liposomes, A Drug Carrier: A Prediction by Differential Scanning Calorimetry," *J. Pharm. Sci.* 84(7):805-813 (1995).

Martonen, T.B., "Mathematical Model for the Selective Deposition of Inhaled Pharmaceuticals", *J. of Pharm. Sci.*, 82(12):1191-1198 (1993).

Masinde, L.E., and Hickey, A.J., "Aerosolized Aqueous Suspensions of Poly(L-Lactic Acid) Microspheres," *Int. J. of Pharmaceutics*, 100:123-131 (1993).

Mathiowitz, E., et al., "Novel Microcapsules for Delivery Systems," *Reactive Polymers*, 6:275-283 (1987).

Mathiowitz, E., et al., "Polyanhydride Microspheres. IV. Morphology and Characterization of Systems Made by Spray Drying," *J. of Appl. Polymer Sci.* 45:125-134 (1992).

Mathiowitz, E., et al., "Morphology of Polyanhydride Microsphere Delivery Systems," *Scanning Microscopy*, 4(2):329-340 (1990).

Mathiowitz, E., and R. Langer, "Polyanhydride Microspheres as Drug Carriers I. Hot-Melt Microencapsulation," *J. of Controlled Release* 5:13-22 (1987).

Mathiowitz, E., et al., "Polyanhydride Microspheres as Drug Carriers. II. Microencapsulation by Solvent Removal," *J. of Appl. Polymer Sci.*, 35:755-774 (1988).

Ménache, M.G., et al., "Particle Inhalability Curves for Humans and Small Laboratory Animals," *Annals of Occupational Hygiene*, 39(3):317-328 (1995).

Morén, F., "Aerosol Dosage Forms and Formulations," in *Aerosols in Medicine. Principles, Diagnosis and Therapy*, Morén, et al., Eds, Elsevier, Amsterdam, 1985.

Morimoto, Y., and Adachi, Y., "Pulmonary Uptake of Liposomal Phosphatidylcholine Upon Intratracheal Administration to Rats," *Chem. Pharm. Bull.* 30(6):2248-2251 (1982).

Mulligan, R.C., "The Basic Science of Gene Therapy", *Science*, 260:926-932 (1993).

Mumenthaler, M., et al., "Feasibility Study on Spray-Drying Protein Pharmaceuticals: Recombinant human Growth Hormone and Tissue-Type Plasminogen Activator," *Pharm. Res.*, 11(1):12-20 (1994). This reference number intentionally left blank.

Newman, S.P., "Therapeutic Inhalation Agents and Devices," *Inhalation Therapy*, 76(5):194-207 (1984).

Newman, S.P., "Aerosol Deposition Considerations in Inhalation Therapy," *Chest*, 88(2):152S-160S (1985).

Niven, R.W., et al., "The Pulmonary Absorption of Aerosolized and Intratracheally Instilled rhG-CSF and monoPEGylated rhG-CSF," *Pharm. Res.*, 12(9):1343-1349 (1995).

Niven, R.W., et al., "Solute Absorption From the Airways of the Isolated Rat Lung. III. Absorption of Several Peptidase-Resistant, Synthetic Polypeptides: Poly-(2-Hydroxyethyl)-Aspartamides," *Pharm. Res.*, 7(10):990-994 (1990).

Niwa, T., et al., "Aerosolization of Lactice/Glycolide Copolymer (PLGA) Nanospheres for Pulmonary Delivery of Peptide-Drugs," *Yakugaku Zasshi*, 115(9):732-741 (1995).

Ogiwara, M.,"Clearance and Maximum Removal Rate of Liposomes in Normal and Impaired Liver of Rat," *Gastroenterologia Japonica*, 19(1):34-40 (1984).

Okumura, K., et al., "Intratracheal Delivery of Insulin. Absorption from Solution and Aerosol by Rat Lung," *Int. J. Pharmaceutics*, 88:63-73 (1992).

Patton, J.S., and R.M. Platz, "(D) Routes of Delivery: Case Studies (2) Pulmonary Delivery of Peptides and Proteins for Systemic Action", *Adv. Drug Del. Rev.*, 8:179-196 (1992).

Patton, J.S., et al., "Bioavailability of pulmonary delivered peptides and proteins: α-interferon, calcitionins and parathyriod hormones," *J. Controlled Release*, 28:79-85 (1994).

Pavia, D., "Lung Mucociliary Clearance". In *Aerosols and the Lung: Clinical and Experimental Aspects*, Clarke, S.W. and Pavia, D., eds.(Butterworths, London), pp. 127-155, (1984).

Peart, J. et al., "Multicomponent Particle Interactions in Dry Powder Aerosols," *J. Pharm. Res.* 14(11 Suppl):p. S142-S143 (Nov. 1997).

Pinkerton, K.E., et al., "Aerosolized Fluorescent Microsphere Detected in the Lung Using Confocal Scanning Laser Microscopy", *Microscopy Res. and Tech.*, 26:437-443 (1993).

Rudt, S., and R.H. Muller, "In Vitro Phagocytosis Assay of Nano- and Microparticles by Chemiluminescence. I. Effect of Analytical Parameters, Particle Size and Particle Concentration," *J. Contr. Rel.*,22:263-271 (1992).

Rudt, S., et al., "In Vitro Phagocytosis Assay of Nano- and Microparticles by Chemiluminescence. IV. Effect of Surface Modification by Coating of Particles with Poloxamine and Antarox CO on the Phagocytic Uptake", *J. of Contr. Rel.* 35:123-132 (1993).

Ruffin, R.E., et al., "The Preferential Deposition of Inhaled Isoproterenol and Propranolol in Asthmatic Patients," *Chest* 80(6):904-907 (1981).

Sela, M., et al., "Multichain Polyamino Acids," *J. Am. Chem. Soc.*, 78:746-751 (1956).

Smith, A.L., and B. Ramsey, "Aerosol Administration of Antibiotics," *Respiration*, 62(suppl 1):19-24 (1995).

Smith, P.L., "Peptide Delivery via the Pulmonary Route: A Valid Approach for Local and Systemic Delivery," *J. of Contr. Rel.*, 46:99-106 (1997).

Strand, S.E., and L. Bergqvist, "Radiolabeled Colloids and Macromolecules in the Lymphatic System," *Critical Reviews in Therapeutic Drug Carrier Systems*, 6(3):211-238 (1989).

Swift, D., "The Oral Airway—A Conduit or Collector for Pharmaceutical Aerosols?" *Respiratory Drug Delivery IV*, 187-195 (1994).

Tabata, Y., et al., "Controlled Delivery Systems for Proteins Using Polyanhydride Microspheres," *Pharm. Res.* 10(4):487-496 (1993).

Tabata, Y., and Y. Ikada, "Effect of Surface Wettability of Microspheres on Phagocytosis," *J. of Colloid and Interface Sci.*, 127(1):132-140 (1989).

Tabata, Y., and Y. Ikada, "Macrophage Phagocytosis of Biodegradable Microspheres Composed of L-lactic Acid/glycolic Acid Homo- and Copolymers," *J. of Biomed. Mater. Res.*, 22:837-858 (1988).

Tabata, Y., and Ikada, Y., "Effect of Size and Surface Charge of Polymer Microspheres on Their Phagocytosis by Macrophage," *J. Biomed. Mater. Res.*, 22:837-843 (1988).

Taburet, A.M., and Schmit, B., "Pharmacokinetic Optimisation of Asthma Treatment," *Clin. Pharmacokinet.*26(5):396-418 (1994).

Tansey, I.P., "Challenges in the Development of Metered Dose Inhalation Aerosols Using Ozone-Friendly Propellants," *Spray Technol. & Market*, 4:26-29 (1994).

Timsina, M.P., et al., "Drug Delivery to the Respiratory Tract Using Dry Powder Inhalers," *Int. J. of Pharm.*, 101:1-13 (1994).

Turner, J. R., and S.V. Hering, "Greased and Oiled Substrates as Bounce-Free Impaction Surfaces," *J. Aerosol Sci.*, 18(2):215-224 (1987).

Visser, J., "An Invited Review: Van der Waals and Other Cohesive Forces Affecting Power Fludization, " Powder Technology, 58:1-10 (1989).

Wall, D.A., "Pulmonary Absorption of Peptides and Proteins," *Drug Delivery*, 2:1-20 (1995).

Warheit, D.B., and Hartsky, M.A., "Role of Alveolar Macrophage Chemotaxis and Phagocytosis in Pulmonary Clearance to Inhaled Particles: Comparisons Among Rodent Species," *Microscopy Res. and Tech.*, 26:412-422 (1993).

Weiner, Norman et al., "Liposomes as a Drug Delivery System," *Drug Development and Industrial Pharmacy*, 15(10):1523-1554 (1989).

Wheatley,M.A., et al., "Contrast Agents for Diagonostic Ultrasound: Development and Evaluation of Polymer-Coated Microbubbles," *Biomaterials* 11:713-717 (1990).

Wichert, B., and Rohdewald, P., "Low Molecular Weight PLA: A Suitable Polymer for Pulmonary Administered Microparticles?," *J. Microencapsulation*, 10(2):195-207 (1993).

Wong, M., and Suslick, K.S., "Sonochemically Produced Hemoglobin Microbubbles," *Mat. Res. Soc. Symp. Proc.*, 372:89-95 (1995).

Zanen, P., et al., "The Optimal Particle Size for β-adrenergic Aerosols in Mild Asthmatics", *Int. J. of Pharm.*, 107:211-217 (1994).

Zanen, P., et al., "The Optimal Particle Size for Parasympathicolytic Aerosols in Mild Asthmatics", *Int. J. of Pharm.*, 114:111-115 (1995).

Zeng, X.M., et al., "The Controlled Delivery of Drugs to the Lung," *Int. J. of Pharm.*, 124:149-164 (1995).

Zeng, X.M., et al., "Tetrandrine Delivery to the Lung: The Optimisation of Albumin Microsphere Preparation by Central Composite Design," *Int. J. of Pharm.*, 109:135-145 (1994).

PARTICULATE COMPOSITIONS FOR PULMONARY DELIVERY

RELATED APPLICATIONS

This application is a continuation of U.S. application Ser. No. 10/300,657, filed Nov. 20, 2002 now U.S. Pat. No. 7,182,961, which claims the benefit of U.S. Provisional Application No. 60/331,708, filed on Nov. 20, 2001. The entire teachings of the above applications are incorporated herein by reference.

BACKGROUND OF THE INVENTION

Previously Applicants have found that dry powder comprising aerodynamically light particles are suitable for inhalation of drugs into the lungs. However, there are several problems associated with the aerosol delivery of therapeutic, diagnostic and/or prophylactic agents (hereinafter collectively referred to as drug). For example, electrostatic charge interactions influence the overall efficiency of delivery of dry particles via a Dry Powder Inhaler (DPI), since such forces are considered to be significant for attraction and adhesion between the particles themselves as well as between the particles and the device surface. Additionally, particle size distribution, particle morphology, and moisture content can greatly influence the bulk properties of a dry powder formulation and its performance.

In the case of dry powders comprising aerodynamically light particles, appropriate criteria and tests must be instituted to control parameters considered to be key to ensuring reproducibility of the physicochemical properties of the drug containing particles. Key specification parameters may include color, appearance (visual and microscopic), moisture, melting range, particle size distribution, surface area, form(s), and residual solvents. Specifications for control of particle size distribution and forms (e.g., shape, texture, surface) of the drug containing particles are parameters often used to predict reproducible drug product performance.

The composition of a formulation to be administered via a DPI has a direct effect on the stability of the formulation as well as on the dosing performance of the product. The suitability of a dry powder particulate composition is dependent on its chemical and physical characteristics, which can have direct effect on the performance of the product (e.g., ease of entrainment of the formulation, energy input necessary for dispersion and aerosolization, hygroscopicity of the formulation). For example, aggregation of dry powder particles may affect the particle size distribution of the emitted drug substance, the homogeneity of the drug substance, the aerodynamic properties of the dry powder particles in the device, and hence the delivered dose.

For DPI's, the target formulation fill weight is important yet it can be deceptive if the particle delivery is variable due to varying levels of aggregation of cohesive particles. Particles produced for inhalation, which are typically small in size (geometric diameter of 1 to 5 μm), tend to stick together.

Edwards et al. (U.S. Pat. No. 5,985,309) (hereinafter referred to as "Edwards") discloses advantages of aerodynamically light particles for drug delivery to the pulmonary system. Edwards use of larger particles (i.e., mass median diameter of at least about 5 microns) is advantageous since they are able to aerosolize more efficiently than smaller, denser aerosol particles such as those currently used for inhalation therapies.

Thus, there is a need for improved pharmaceutical compositions suitable for pulmonary administration delivered via a dry powder inhaler with improved aerosolization properties and optimized particle-particle interactions. In particular, there is a need for dry powder pharmaceutical compositions which are highly dispersible and which efficiently emit and penetrate into the lungs from a dry powder inhaler.

SUMMARY OF THE INVENTION

This invention concerns an improved particulate composition for delivering a drug to the pulmonary system. A drug may be a therapeutic, diagnostic and/or prophylactic agent. Applicants disclose a method of identifying an optimal form of aerodynamically light particles which are highly dispersible. The particles of the instant invention are made by creating hollow, spherical drug particles (i.e., progenitor particles) that collapse in the process of particle formation, leading to wrinkled, thin-walled drug particles of very low envelope density. Additionally, Applicants have found that such particles are especially optimal for inhaled aerosols when the surface area parameter ($\sigma$) is greater than 2, optimally greater than 3.

The invention relates to an improved particulate composition for pulmonary system comprising particles having a tap density of less than 0.4 $g/cm^3$ and a median geometric diameter greater than 5 μm, and an external surface area greater than about 5 $m^2/g$, preferably greater than about 10 $m^2/g$. In a further embodiment, the particles further comprise a drug. In another embodiment, the particles further comprise a pharmaceutical excipient. In yet another embodiment, the particles further comprise a dispersibility ratio of between about 1.0 to 1.5 as measured by laser diffraction (RODOS/HELOS system). In a further embodiment, the particles have a skeletal density of at least 1 $g/cm^3$.

In another embodiment, the invention relates to an improved particulate composition for delivery of a drug to the pulmonary system comprising particles having a tap density of less than 0.4 $g/cm^3$ and a geometric diameter greater than 5 μm, said particles having a continuous collapsed hollow sphere wall, said wall having a wall thickness less than about 150 nanometers and an external surface area of at least 5 $m^2/g$. In a further embodiment, at least 70% of the particles of the particulate composition have a fine particle fraction of less than 5.6 μm.

In another embodiment, the invention relates to a method for maximizing drug delivery to the pulmonary system comprising: a) spray drying a mixture comprising the drug and a pharmaceutically acceptable excipient to form spray dried particles; b) measuring an average wall thickness of the spray dried particles; c) adjusting spray drying conditions to minimize the average wall thickness; d) collecting spray dried particles having minimized average wall thickness; and e) administering spray dried particles having minimized average wall thickness to the respiratory tract of a patient in need of the drug.

BRIEF DESCRIPTION OF THE DRAWINGS

The foregoing and other objects, features and advantages of the invention will be apparent from the following more particular description of preferred embodiments of the invention, as illustrated in the accompanying drawings in which like reference characters refer to the same parts throughout the different views. The drawings are not necessarily to scale, emphasis instead being placed upon illustrating the principles of the invention.

DEFINITIONS

Figure 1:
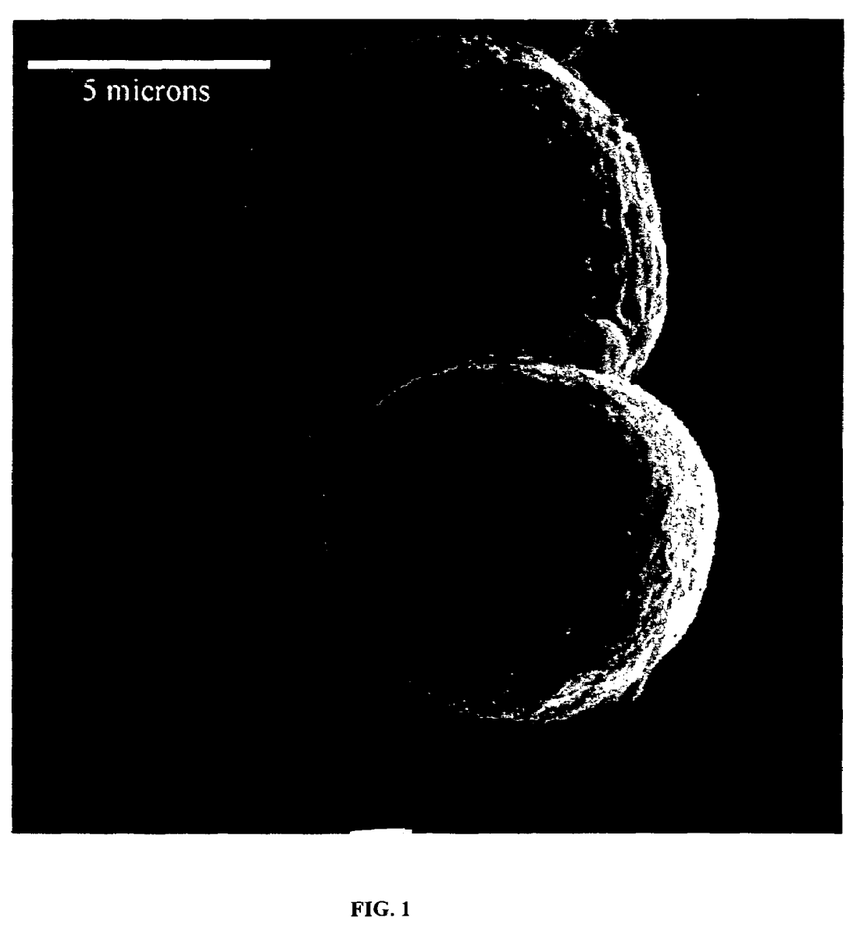
FIG. 1 is an SEM image of a representative formulation i (spherical paper morphology) powder particle.
Figure 2:
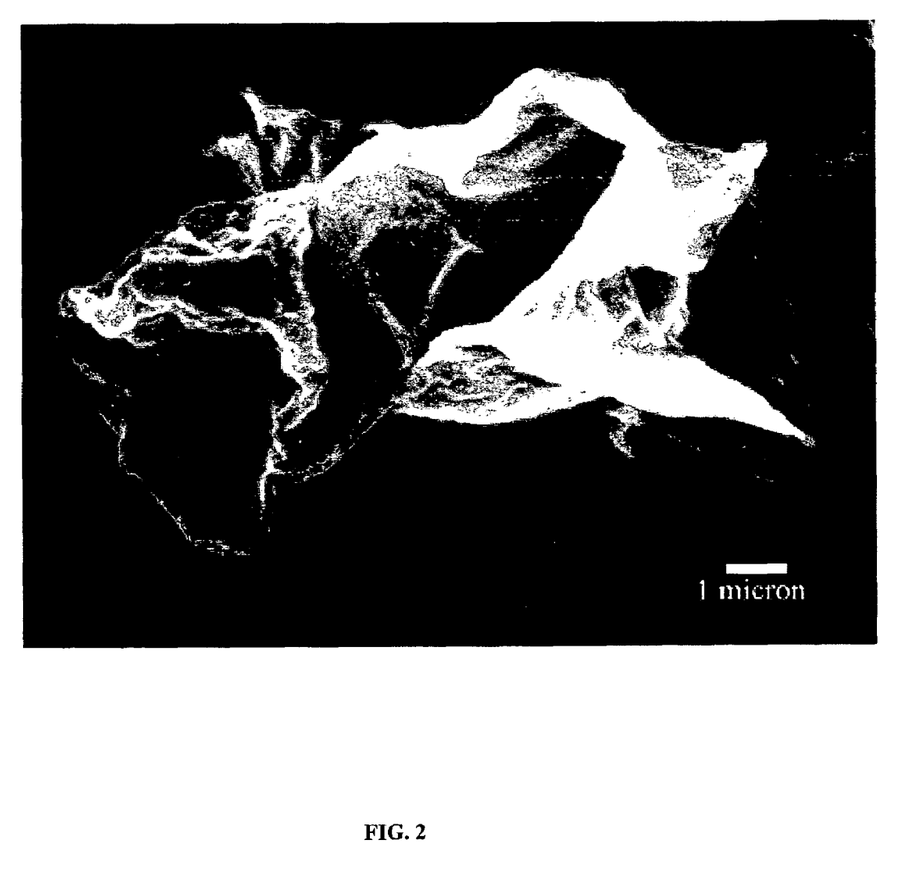
FIG. 2 is an SEM image of a representative formulation ii (crumpled paper morphology) powder particle.
Figure 3A:
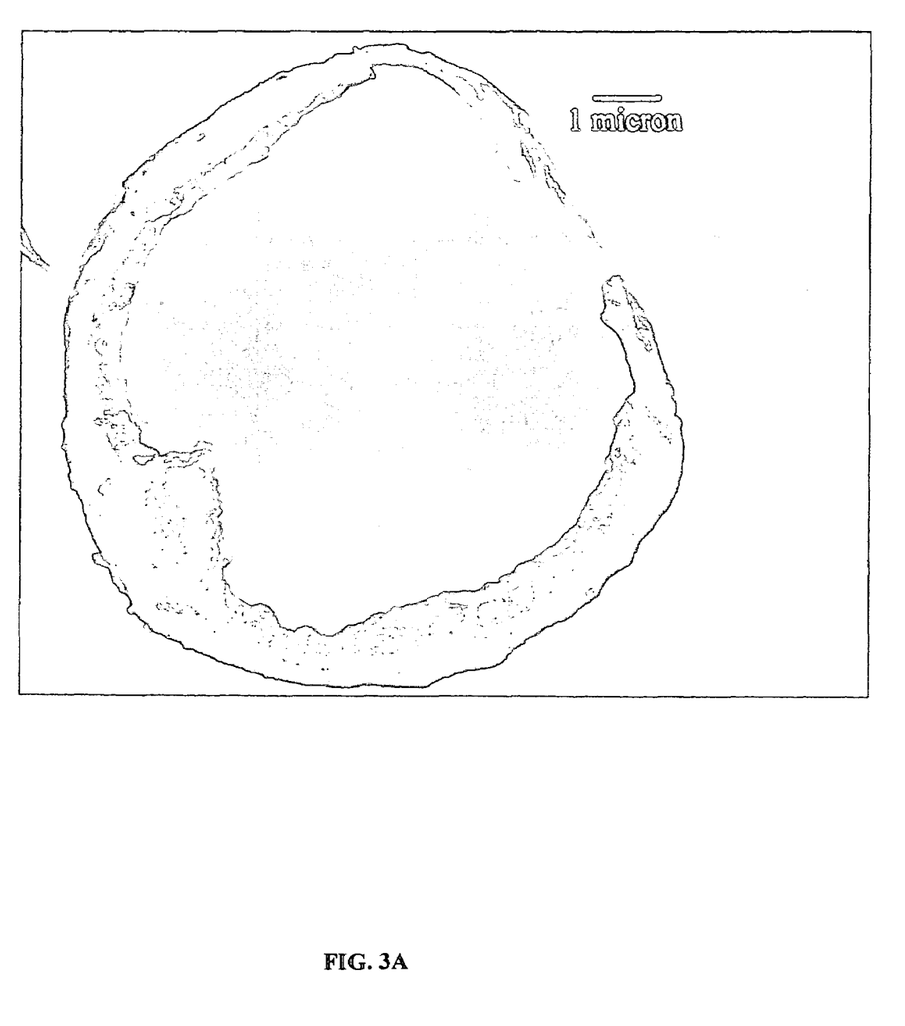
FIGS. 3A and 3B are SEM images showing the wall thickness of a representative formulation i (spherical morphology) powder particle.
Figure 3B:
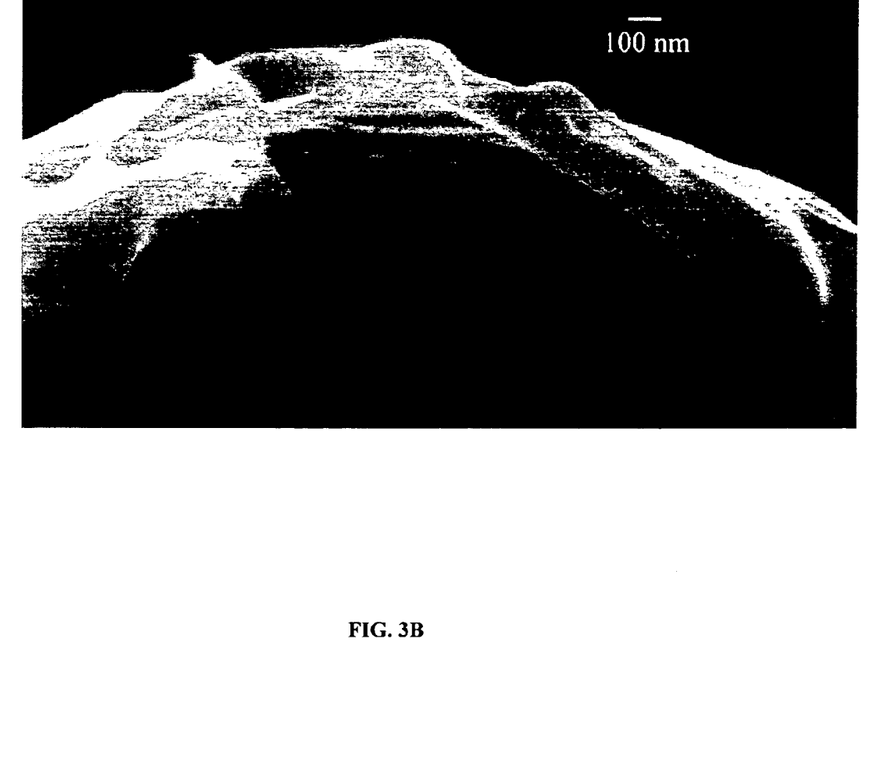
Figure 4:
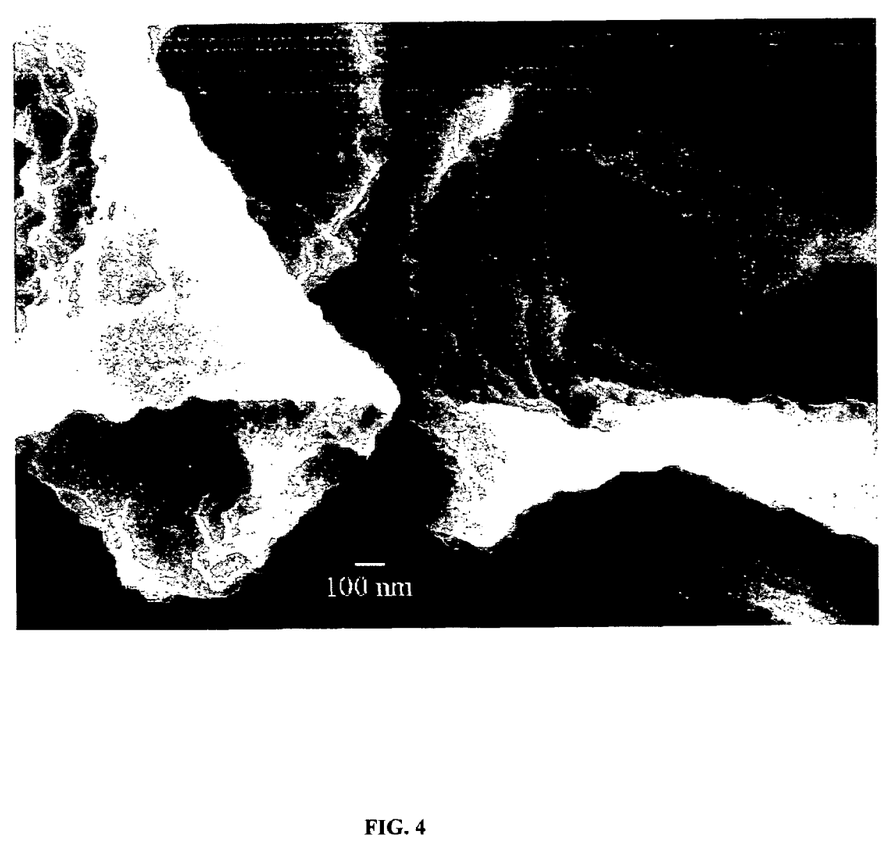
FIG. 4 is an SEM image showing the wall thickness of a representative formulation ii (crumpled paper morphology) powder particle.

As used herein, the term "wall thickness" refers to the average thickness of the wall of a particle. For thin walled particles of the invention, wall thickness is on the order of about 50-150 nm, preferably from about 75 to 125 nm, which is about 1% of the spherical envelope diameter of the particle. Measurement techniques are known to those skilled in the art and include, but are not limited to, visual observations (e.g., SEM, TEM), or are calculated as a function of spherical envelope diameter, tap density and surface area.

As used herein, the term "spherical envelope diameter" refers to the diameter of a sphere that completely encompasses a given particle.

As used herein, the term "envelope density" refers to the ratio of the mass of a particle to the sum of the volumes of the solid in each piece and the voids within each piece, that is, within close-fitting imaginary envelopes completely surrounding each piece. In other words, envelope density refers to the ratio of the mass of a particle to the envelope volume of the particle.

As used herein, the terms "contiguous shell surface" or "shell-based particles", used to describe the particles of the instant invention, refers to hollow particles characterized by a single wall with an internal and an external surface (i.e., balloon-like). The wall is typically considered to be a closed and contiguous surface, although some cracks and/or blowholes can occur. Some particles disclosed in the art have walls that are microporous (sponge-like) in nature and have multiple walls on their interiors and have not been formed from a single shell as defined above.

As used herein, the term "external surface area" refers to the surface area on the exterior side of the contiguous shell surface for particles of the invention. The external surface area of shell-based particles with contiguous solid walls can be measured via techniques know to those of skill in the art that include, but are not limited to, Atomic Force Microscopy (AFM) and BET isotherm analysis. For example, crumpled particles of the invention having a geometric diameter of approximately 10 microns, have external surface areas as measured by BET isotherm analysis of about 12 to about 15 square meters per gram. This is a value of approximately twice the external surface area of a smooth, spherical particle of the same spherical envelope diameter and tap density as the crumpled particle. A range of external surface area for particles of the invention is from about 5 to about 50 square meters/gram. Preferably, a range of external surface area for particles of the invention is from about 8 to about 25 square meters/gram. More preferably, a range of external surface area for particles of the invention is from about 10 to about 15 square meters/gram.

As used herein, the term "internal surface area" refers to the surface area on the interior side of the contiguous shell surface for particles of the invention. The internal surface area of shell-based particles with contiguous solid walls cannot be measured directly via techniques such as Atomic Force Microscopy (AFM) and BET isotherm analysis, but can be estimated based on the external particle surface area and particle wall thickness. For cases such as those described here involving shell-based particles with wall thicknesses much less than the particle spherical envelope diameter, the internal surface area will be approximately equal to the external surface area.

As used herein, the term "skeletal density" refers to the ratio of the mass of discrete pieces of solid material to the sum of the volumes of the solid material in the pieces and closed (blind) pores within the pieces. The particles of the instant invention have skeletal densities from about 1 to about 1.3 g/cm$^3$, preferably 1.2 g/cm$^3$, which is equivalent to the dense bulk starting material density (phospholipids, etc.), which indicates that the walls of the particles are relatively dense and do not contain encased pores. Measurement techniques are known to those skilled in the art and include, but are not limited to, gas pycnometry (Helium).

DETAILED DESCRIPTION OF THE INVENTION

A description of preferred embodiments of the invention follows.

This invention concerns an improved particulate composition for delivering a drug to the pulmonary system. In particular, the improvement relates to the ideal design of an aerodynamically light particle for inhalation. Specifically, it has been determined that there is a synergistic interrelationship of key characteristics of spray-dried particles that results in an optimal aerodynamic performance of particles for inhaled therapeutic aerosols. This synergy promotes finely crumpled yet structurally-robust particles of low tap density (<0.4 g/cm$^3$) and relatively large particle geometric size (>5 μm) that require less energy to effectively aerosolize than thicker-walled particles of similar size and mass density. Preferably, this design promotes structurally-robust particles of ultra-low tap density (<0.1 g/cm$^3$) and relatively large particle size (>10 μm). Preferred particles are hollow, extremely thin-walled particles comprising drugs and, optionally, excipients. Further, the particles of the invention relative to particles of alternative morphologies (i.e., non-hollow particles), require less energy to produce. By reducing particle wall thickness to around 1% of the particle spherical envelope diameter, it is possible to achieve large drug-surface-transport area without necessarily creating the large particle-particle contact area that underlies handling drawbacks normally associated with nanoparticle drug delivery systems.

It was the discovery of the synergy of the interrelationships of key characteristics that led to improved methods for producing and selecting for particles with superior dispersibility. For example, the focus on key characteristics has led to innovations such as on-line sizing in which a "real-time" feedback loop is possible which can reduce waste and optimize the process for making such superior particles. (See U.S. patent application Ser. No. 10/101,563 with the title "Method and Apparatus for Producing Dry Particles" filed Mar. 20, 2002, under the Attorney Docket No. 00166.0115) This is especially important in the production of high cost drugs, for example, proteins. Thus, these improved compositions have improved dispersibility due to homogeneity of the particles.

Accordingly, the invention relates to an improved particulate composition. The improvement is that when the median aerodynamic diameter, median geometric diameter and tap density of two different contiguous shell-based particulate compositions of the same formulation are kept equal, there exists a synergistic relationship between the external surface area, wall thickness, and skeletal density that leads to preferred Fine Particle Fraction (FPF) and dispersibility/flowability as measured by RODOS, RODOS/ IHA, or both. This synergistic relationship results in superior particles which exhibit better dispersibility with less variability over a wide range of entrainment conditions thereby improving the delivery of the particulate composition.

It is known in the art that spray drying a particle formulation under different "operating" conditions can result in spray-dried particles with various characteristics. However, this invention relates to particles whose performance criteria is tightly controlled to ensure appropriate conformance in other related attributes, for example, particle size, dose content uniformity and lung deposition. Therefore, this invention demonstrates that, although two or more spray-dried powders may have the same median aerodynamic diameter, median geometric diameter and tap density, that altering the spray-drying conditions of one of the spray-dried formulations to optimize the wall thickness and external surface area of the particles results in formulations possessing a larger surface area, and thus roughness, and thinner walls than the other formulations. Applicants further demonstrate that the formulation that has optimized the synergistic relationship among the particle characteristics enhances the dispersibility and flowrate independence for that formulation.

In one embodiment, Applicants disclose a method for selectively modulating the individual factors within an extremely tight range (e.g., within 5% of the mean for the individual factor) without interfering with the synergistic relationship. The resulting particles are able to achieve flowrate independence leading to enhanced dispersibility by selectively choosing those particles that have a large geometric diameter (i.e., >5 µm), a small aerodynamic diameter (i.e., a low density with respect to geometric diameter), a minimum average wall thickness and a large external surface area.

In one embodiment of the instant invention, particles of larger size and the highly convoluted morphology contribute to make them easily dispersable and stable with respect to aggregation during storage. In this embodiment, the particle morphology contributes to enhanced dispersability and stability by decreasing the area of contact between particle. The surface contact is minimized by presence of numerous folds and convolutions. The radially-exposed surface is thus reduced as the particle surface is dominated by crevices which cannot interact chemically during contact with other particles. Particles with diameters of <5 µm are prone to aggregation, with this tendency increasing as diameter decreases.

In one embodiment, the particles can be fabricated with a rough surface texture to reduce particle aggregation and improve flowability of the powder. The spray-dried particles have improved aerosolization properties. The spray-dried particle can be fabricated with features which enhance aerosolization via dry powder inhaler devices, and lead to lower deposition in the mouth, throat and inhaler device.

As used herein, the term "surface area factor" ($\sigma$) refers to the ratio of the external and internal surface area of a shell-based particle or particle formulation to the theoretical surface area of a solid spherical particle or particle formulation with the same spherical envelope diameter and tap density. To calculate the surface area factor of a particle, let S=the surface area of a particle of arbitrary shape so that $\sigma$ is defined as:

$$\sigma = S/(\pi D_e^2)$$

where $D_e$=the spherical envelope diameter of the particle. For example, if the particle is a solid sphere, where the wall thickness (h)=$D_e/2$, $S=\pi D_e^2$, resulting in $\sigma=1$. However, if the particle is a hollow sphere with a wall thickness approaching zero (0), then $S=2\pi D_e^2$, resulting in $\sigma=2$. The invention relates to producing hollow spheres with thin walls (yet having sufficient rigidity to prevent disintegration of the wall) that collapse to form crumpled particles, thereby increasing the surface area factor to values greater than 2.

Thus, the invention therefore involves aerodynamically light particles, with improved dispersibilty, wherein the improvement results by collapsing hollow particles with surface area factor between 1 and 2 ($1<\sigma<2$), to form collapsed particles with surface area factor greater than 2 ($\sigma>2$), ideally greater than 3, and perhaps most ideally greater than 5. The validation of this invention is our finding that drug particles with $1<\sigma<2$ aerosolize less well than particles with $\sigma>2$, all other things being equal.

The increased surface areas of the particle distributions disclosed herein can also be described via estimates of particle rugosity. As defined herein, particle rugosity (R) is the ratio of the ratio of the external surface area of a shell-based particle or particle formulation to the theoretical surface area of a solid spherical particle or particle formulation with the same spherical envelope diameter and tap density. Thus, as described above, for shell-based particle formulations with wall thicknesses significantly less than particle spherical envelope diameters, particle rugosity will be approximately equal to one-half of the surface area factor (i.e., $R = 0.5\sigma$).

In another embodiment of the invention the particles can include a surfactant. As used herein, the term "surfactant" refers to any agent which preferentially adsorbs to an interface between two immiscible phases, such as the interface between water and an organic polymer solution, a water/air interface or organic solvent/air interface. Surfactants generally possess a hydrophilic moiety and a lipophilic moiety, such that, upon absorbing to microparticles, they tend to present moieties to the external environment that do not attract similarly-coated particles, thus reducing particle aggregation. Surfactants may also promote absorption of a therapeutic or diagnostic agent and increase bioavailability of the agent.

Suitable surfactants which can be employed in fabricating the particles of the invention include but are not limited to hexadecanol; fatty alcohols such as polyethylene glycol (PEG); polyoxyethylene-9-lauryl ether; a surface active fatty acid, such as palmitic acid or oleic acid; glycocholate; surfactin; a poloxamer; a sorbitan fatty acid ester such as sorbitan trioleate (Span 85); Tween 80 and tyloxapol.

Methods of preparing and administering particles including surfactants, and in particular phospholipids, are disclosed in U.S. Reissue Pat. No. RE 37,053 to Hanes et al. (formerly U.S. Pat. No 5,855,913, issued on Jan. 5, 1999) and in U.S. Pat. No. 5,985,309, issued on Nov. 16, 1999 to Edwards et al. The teachings of both are incorporated herein by reference in their entirety.

In a further embodiment, the particles can also include other excipients such as, for example buffer salts, dextran, polysaccharides, lactose, trehalose, cyclodextrins, proteins, polycationic complexing agents, peptides, polypeptides, fatty acids, fatty acid esters, inorganic compounds, phosphates, lipids, sphingolipids, cholesterol, surfactants, polyaminoacids, polysaccharides, proteins, salts, gelatins, polyvinylpyrridolone and others also can be employed.

In another embodiment, the particles of the invention can include one or more phospholipids. Phospholipids suitable for delivery to a human subject are preferred. Specific examples of phospholipids include but are not limited to phosphatidylcholines dipalmitoyl phosphatidylcholine (DPPC), dipalmitoyl phosphatidylethanolamine (DPPE), distearoyl phosphatidylcholine (DSPC), dipalmitoyl phosphatidyl glycerol (DPPG) or any combination thereof.

The phospholipids or combinations thereof and methods of preparing particles having desired release properties are described in U.S. patent application Ser.No. 09/752,106, entitled "Particles for Inhalation Having Sustained Release Properties", filed on Dec. 29, 2000, in U.S. patent application Ser. No. 09/752,109, entitled "Particles for Inhalation Having Sustained Release Properties", filed on Dec. 29, 2000, and in U.S. patent application entitled "Inhaled Formulations for Sustained Release", filed on concurrently herewith under Attorney Docket No. 2685.2032-001; the entire contents of these three applications are incorporated herein by reference.

The phospholipids can be present in the particles in an amount ranging from about 1 to about 99 weight %. Preferably, they can be present in the particles in an amount ranging from about 10 to about 80 weight %.

In one embodiment, the particles of the invention have a tap density less than about 0.4 g/cm$^3$. Particles which have a tap density of less than about 0.4 g/cm$^3$ are referred herein as "aerodynamically light particles". More preferred are particles having a tap density less than about 0.3 g/cm$^3$. Even more preferred are particles having a tap density less than about 0.2 g/cm$^3$. Preferably, the particles have a tap density less than about 0.1 g/cm$^3$. Tap density can be determined using the method of *USP Bulk Density and Tapped Density*, United States Pharmacopeia convention, Rockville, Md., 10$^{th}$ Supplement, 4950-4951, 1999. Instruments for measuring tap density, known to those skilled in the art, include but are not limited to the Dual Platform Microprocessor Controlled Tap Density Tester (Vankel, N.C.) or a GeoPyc instrument (Micrometrics Instrument Corp., Norcross, Ga. 30093). Tap density is a standard measure of the envelope mass density. The envelope mass density of an isotropic particle is defined as the mass of the particle divided by the minimum spherical envelope volume within which it can be enclosed. Features which can contribute to low tap density include irregular surface texture and porous structure.

Aerodynamically light particles have a preferred size, e.g., a volume median geometric diameter (VMGD) greater than about 5 microns (μm). In one embodiment, the VMGD is from greater than about 5 μm to about 30 μm. In another embodiment of the invention, the particles have a VMGD ranging from about 10 μm to about 30 μm. In a preferred embodiment, the particles have a VMGD greater than about 5 μm. Even more preferred are particles having a VMGD greater than about 8 μm. Most preferred are particles having a VMGD greater than about 10 μm. In other embodiments, the particles have a median diameter, mass median diameter (MMD), a mass median envelope diameter (MMED) or a mass median geometric diameter (MMGD) greater than about 5 μm, for example from greater than about 5 μm and about 30 μm.

The diameter of the spray-dried particles, for example, the VMGD, can be measured using a laser diffraction instrument (for example Helos, manufactured by Sympatec, Princeton, N.J.). Other instruments for measuring particle diameter are well known in the art. The diameter of particles in a sample will range depending upon factors such as particle composition and methods of synthesis. The distribution of size of particles in a sample can be selected to permit optimal deposition to targeted sites within the respiratory tract.

Aerodynamically light particles preferably have "mass median aerodynamic diameter" (MMAD), also referred to herein as "aerodynamic diameter", between about 1 μm and about 5 μm. In another embodiment of the invention, the MMAD is between about 1 μm and about 3 μm. In a further embodiment, the MMAD is between about 3 μm and about 5 μm.

Other suitable particles which can be adapted for use in oral delivery as described herein, said particles being described in U.S. patent application "Particulate Compositions for Improving Solubility of Poorly Soluble Agents" (Attorney Docket No.: 2685.2014-001) and U.S. patent application "Compositions for Sustained Action Product Delivery and Methods of Use Thereof" (Attorney Docket No.: 2685.2006-002) filed concurrently herewith and incorporated in their entirety by reference herein.

The dosage to be administered to the mammal, such as a human, will contain a therapeutically effective amount of a compound described herein.

As used herein, the term "therapeutically effective amount" means the amount needed to achieve the desired therapeutic or diagnostic effect or efficacy when administered to the respiratory tract of a subject in need of treatment, prophylaxis or diagnosis. The actual effective amounts of drug can vary according to the biological activity of the particular compound employed; specific drug or combination thereof being utilized; the particular composition formulated; the mode of administration; the age, weight, and condition of the patient; the nature and severity of the symptoms or condition being treated; the frequency of treatment; the administration of other therapies; and the effect desired. Dosages for a particular patient can be determined by one of ordinary skill in the art using conventional considerations, (e.g. by means of an appropriate, conventional pharmacological protocol).

In one embodiment of the invention, delivery to the pulmonary system of particles is by the methods described in U.S. patent application, High Efficient Delivery of a Large Therapeutic Mass Aerosol, application Ser. No. 09/591,307, filed Jun. 9, 2000, and U.S. patent application, Highly Efficient Delivery of A Large Therapeutic Mass Aerosol, application Ser. No. 09/878,146, filed Jun. 8, 2001. The entire contents of both these applications are incorporated herein by reference. As disclosed therein, particles are held, contained, stored or enclosed in a receptacle. Preferably, the receptacle, e.g. capsule or blister, has a volume of at least about 0.37 cm$^3$ and can have a design suitable for use in a dry powder inhaler. Larger receptacles having a volume of at least about 0.48 cm$^3$, 0.67 cm$^3$ or 0.95 cm$^3$ also can be employed.

The methods of the invention also relate to administering to the respiratory tract of a subject, particles and/or compositions comprising the particles of the invention, which can be enclosed in a receptacle. As described herein, in certain embodiments, the invention is drawn to methods of delivering the particles of the invention, while in other embodiments, the invention is drawn to methods of delivering respirable compositions comprising the particles of the invention. As used herein, the term "receptacle" includes but is not limited to, for example, a capsule, blister, film covered container well, chamber and other suitable means of storing particles, a powder or a respirable composition in an inhalation device known to those skilled in the art.

The invention is also drawn to receptacles which are capsules, for example, capsules designated with a particular capsule size, such as 2, 1, 0, 00 or 000. Suitable capsules can be obtained, for example, from Shionogi (Rockville, Md.). Blisters can be obtained, for example, from Hueck Foils, (Wall, N.J.). Other receptacles and other volumes thereof suitable for use in the instant invention are known to those skilled in the art.

Suitable organic solvents that can be employed include but are not limited to alcohols for example, ethanol, methanol, propanol, isopropanol, butanols, and others. Other organic solvents include but are not limited to perfluorocarbons, dichloromethane, chloroform, ether, ethyl acetate, methyl tert-butyl ether and others.

Suitable spray-drying techniques are described, for example, by K. Masters in "Spray Drying Handbook", John Wiley & Sons, New York, 1984. Generally, during spray-drying, heat from a hot gas such as heated air or nitrogen is used to evaporate the solvent from droplets formed by atomizing a continuous liquid feed. Other spray-drying techniques are well known to those skilled in the art. In a preferred embodiment, a rotary atomizer is employed. Examples of suitable spray driers using rotary atomization include the Mobile Minor spray drier, manufactured by Niro, Denmark. The hot gas can be, for example, air, nitrogen or argon.

Methods and apparatus suitable for forming particles of the present invention are described in U.S. patent application Ser. No. 10/101,536 with the title "Method and Apparatus for Producing Dry Particles" filed Mar. 20, 2002, under the Attorney Docket No. 00166.0115-US00, in U.S. patent application Ser. No. 09/837,620 with the title "Control of Process Humidity to Produce Large, Porous Particles" filed Apr. 18, 2001, and in U.S. patent application Ser. No. 09/383,054 with the title "Stable Spray-Dried Protein Formulations" filed Aug. 25, 1999; the entire contents of these three applications are incorporated by reference herein.

Particles of the invention are suitable for delivery to the pulmonary system. Preferably, particles administered to the respiratory tract travel through the upper airways (oropharynx and larynx), the lower airways which include the trachea followed by bifurcations into the bronchi and bronchioli and through the terminal bronchioli which in turn divide into respiratory bronchioli leading then to the ultimate respiratory zone, the alveoli or the deep lung. In a preferred embodiment of the invention, most of the mass of particles deposits in the deep lung or alveoli.

"Flowability" refers to a powder characteristic that affects the ease of processing. For a material to be considered to be suitably flowable, it must be amenable to processing in automated equipment (such as capsule fillers or tablet making machines) using industry standard techniques. Flowability is measured using a number of techniques referred to as powder rheometric methods such as shear cell methods and dynamic angles of repose.

"Wettability" and "hydroscopicity", can be used interchangably herein, and is a property that affects the interaction of the powder in water. Wettability is a function of surface properties such as surface energy (surface tension) and morphology. This property can be measured using instruments such as dynamic vapor sorption or BET analyzers. Suitable units include water % weight gain.

Powder dispersibility indicators can be obtained via geometric and aerodynamic analytical methods. Geometric size was obtained via laser diffraction (Sympatec RODOS system), with measurements taken at different dispersion pressures used as an indicator of powder dispersibility (e.g, dispersion pressures ranging from 0.25 to 4 bar). The RODOS system can also be used in conjunction with an inhaler attachment system to measure particle size as a function of flowrate (30-90 L/min) through an inhaler, providing another indicator of powder dispersibility. Aerodynamic size distributions of the particles can be obtained via an Aerosizer system utilizing an Aerodisperser (API, Amherst, Mass.).

In a preferred embodiment, the ratio of the sizes obtained at low (0.25 bar) and high (2.0 bar) dispersion pressures (0.25/2 ratio) can be used as an indicator of dispersibility. For example, if a dry powder particle formulation has a 0.25/2 ratio of 3, then the size of the particles measured at low dispersion pressures is three times the size of the particles measured at high dispersion pressures, indicating high levels of particle aggregation at low dispersion pressures. In contrast, if a dry powder particle formulation has a 0.25/2 ratio close to 1, then the size of the particles measured at low dispersion pressures is almost the same as the size of the particles measured at high dispersion pressures, indicating low levels of particle aggregation at low dispersion pressures and flowrate independence.

Similarily, an inhaler to be tested can be attached to the RODOS apparatus (RODOS/IHA) to simulate the conditions under which a powder is emitted from the inhaler. The ratio of the sizes of the powder emitted from an inhaler at low (30 L/min) and high (90 L/min) flowrates (30/90 ratio) can be used as an indicator of dispersibility under clinically relevant conditions. For example, if a dry powder particle formulation has a 30/90 ratio of 3, then the geometric size of the particles measured at low flowrates is three times the size of the particles measured at high flowrates, indicating high levels of particle aggregation at low flowrates. In contrast, if a dry powder particle formulation has a 30/90 ratio close to 1, then the geometric size of the particles measured at low flowrates is almost the same as the size of the particles measured at high flowrates, indicating low levels of particle aggregation at low flowrates, and, thus, enhanced dispersibility and flowrate independence for these particles.

In a prefered embodiment, the invention relates to a method of producing and selecting for particles having a 0.25/2 RODOS ratio that is the same as/similar to the RODOS/IHA 30/90 ratio. The 0.25/2 ratio provides an indication of powder dispersibility under laboratory conditions, whereas the RODOS/IHA 30/90 ratio provides an indication of powder dispersibility under clinical/therapeutic conditions. Thus, by selecting for particles that have a high correlation between these respective ratios one is able to identify compositions with enhanced dispersibility properties.

In a further embodiment, Applicants disclose the increased dispersibility of dry powder particle formulations possessing crumpled morphologies over spherical morphology powder formulations with comparable primary particle geometric and aerodynamic sizes. The critical differences between the particle formulations are based on their morphologies, with the crumpled particles possessing larger surface areas and thinner walls than the spherical particles (these differences in surface areas and wall thicknesses are confirmed in the examples below).

Exemplification

EXAMPLE 1

Production of Particles with Identical Compositions and Differing Morphologies (Spherical vs. Crumpled Paper)

Formulations consisting of 60:20:20 wt:wt dipalmitoylphosphatidylcholine (DPPC, Avanti Polar Lipids, Alabaster, Ala.):bovine serum albumin (BSA, Sigma Chemical Co., St. Louis, Mo.):lactose (Spectrum Chemical Co.,) were spray-dried in the following manner.

via laser diffraction (Sympatec RODOS system), with measurements taken at different dispersion pressures used as an indicator of powder dispersibility (experiments were conducted at dispersion pressures ranging from 0.25 to 4 bar. The RODOS system was also used in conjunction with an inhaler attachment system to measure particle size as a function of flowrate (30-90 l/min) through an inhaler, providing another indicator of powder dispersibility.

Aerodynamic size distributions of the particles were obtained via an Aerosizer system utilizing an Aerodisperser (API, Amherst, Mass.). The results of the geometric, aerodynamic and dispersibility characterization measurements (all data is given in microns) are displayed in Table 1.

| Powder Type | RODOS Size Measurements | | | | | | RODOS - Inhaler Attachment | | | | Aerosizer MMAD |
|---|---|---|---|---|---|---|---|---|---|---|---|
| | 0.25 bar | 0.5 bar | 1 bar | 2 bar | 4 bar | 0.25/2 ratio | 30 l/min | 60 l/min | 90 l/min | 30/90 ratio | |
| i. Spherical | 24.6 | 17.7 | 15.2 | 12.3 | 8.57 | 2.0 | 23.5 | 16.1 | 12.1 | 1.94 | 3.20 |
| ii. Crumpled | 10.6 | 10.3 | 9.91 | 9.50 | 8.80 | 1.12 | 10.1 | 9.90 | 9.65 | 1.05 | 3.14 | i. Production of particles with spherical morphologies. A Niro Mobile Minor Spray Dryer (Niro Inc., Columbus, Md.) equipped with a four vein (V4) rotary atomizer was utilized for powder production. Ethanol:water (70:30 vol:vol) solutions of 4.0 g/l concentrations were utilized for excipient solubilization. For a typical 1 liter batch size, 600 mg DPPC was added to 700 ml of ethanol, and 200 mg of BSA and 200 mg of lactose were added to 300 ml of water (pH adjusted to 8.1 via addition of 1.0 N NaOH after addition of the excipients). The spray drying conditions were as follows: 120° C. inlet temperature, 52,000 RPM atomizer spin rate, 70 ml/min solution feed rate, 108 m3/hr drying gas flow rate (Nitrogen). These conditions resulted in outlet temperatures in the range of 53-55° C. Utilizing a cyclone for powder collection, typical run yields were approximately 40%.

ii. Production of particles with crumpled paper morphologies. A Niro Mobile Minor Spray Dryer (Niro Inc., Columbus, Md.) equipped with a twenty-four vein (V24) rotary atomizer was utilized for powder production. Ethanol:water (85:15 vol:vol) solutions of 1.0 g/l concentrations were utilized for excipient solubilization. For a typical 1 liter batch size, 600 mg DPPC was added to 850 ml of ethanol, and 200 mg of BSA and 200 mg of lactose were added to 150 ml of water (pH adjusted to 8.1 via addition of 1.0 N NaOH after addition of the excipients). The spray drying conditions were as follows: 100° C. inlet temperature, 18,000 RPM atomizer spin rate, 52 ml/min solution feed rate, 100 m3/hr drying gas flow rate (Nitrogen). These conditions resulted in outlet temperatures in the range of 53-55° C. Utilizing a cyclone for powder collection, typical run yields were approximately 40%.

EXAMPLE 2

Powder Geometric and Aerodynamic Property Characterization

Powders produced via methods i and ii from Example 1 above were characterized for their geometric and aerodynamic properties. Powder dispersibility indicators (described below) were also obtained via geometric and aerodynamic analytical methods. Geometric size was obtained The results shown in Table 1 clearly demonstrate the increased dispersibility of the powder formulations possessing crumpled paper morphologies over spherical morphology powder formulations with comparable primary particle geometric and aerodynamic sizes. Using the RODOS results obtained with a dispersion pressure of 4 bar, the spherical (i) and crumpled paper (ii) particle formulations appear to have similar dispersed particle sizes (8.57 microns for i vs 8.80 microns for ii). Additionally, the spherical (i) and crumpled paper (ii) particle formulations appear to have comparable aerodynamic diameters as measured via the Aerosizer (3.20 microns for i vs. 3.14 microns for ii), which also indicates that the particle formulations have comparable particle densities. Estimations of particle densities based on the measured RODOS geometric sizes at 4 bar and the MMADs are 0.14 g/cm$^3$ for formulation i and 0.13 g/cm$^3$ for formulation ii. Thus, the main differences between particle formulations i and ii are based on their morphologies, with the formulation ii particles possessing larger surface areas and roughness and thinner walls than the spherical formulation i particles (these differences in surface areas and wall thicknesses are confirmed in the examples below).

As evidenced by the results shown in Table 1, the crumpled paper particle formulation is significantly more dispersible than the spherical paper particle formulation. For example, the ratio of the size obtained via the RODOS system is highly dependent on the dispersion pressure for the formulation i (spherical) particles, with particle aggregation evident at low dispersion pressures. As shown in Table 1, the ratio of the sizes obtained at low (0.25 bar) and high (2.0 bar) dispersion pressures (0.25/2 ratio) can be used as an indicator of dispersibility. The formulation i (spherical) powder has a 0.25/2 ratio of 2, with the size measured at low dispersion pressures being two times the size measured at high dispersion pressures. In contrast, the 0.25/2 ratio for the formulation ii powder (crumpled) is only 1.12, indicating low levels of particle aggregation at low dispersion pressures.

The RODOS/Inhaler attachment results confirm the enhanced dispersibility of the formulation ii (crumpled) powder as emitted from an inhaler at different flowrates. As shown in Table 1 above, the ratio of measured sizes at flowrates of 30 vs. 90 liters per minute is nearly equal to 2 for the formulation i (spherical) powder, whereas the ratio for the formulation ii (crumpled) powder is close to 1, indicating enhanced dispersibility and flow rate independence for the crumpled paper morphology powder.

EXAMPLE 3

SEM Imaging of Particle Morphology and Wall Thickness

SEM microscopy was utilized to both elucidate the differences in morphology between crumpled paper and spherical morphology powder samples and to confirm that the crumpled paper morphology powder samples possessed thinner walls than the spherical morphology samples. SEM images of samples of the unaltered powders are displayed in FIGS. 1 (formulation i) and 2 (formulation ii). For observation of wall thicknesses, the spherical powders were ground via the use of a 3" diameter cyclone in order to fracture some of the particles to enable imaging of wall cross sections, whereas wall thicknesses were estimated for the crumpled paper morphology powders by observation of tightly folded regions (with the assumption that the wall thickness is approximately ½ the width of the tightly folded region). Estimates for the wall thicknesses were approximately 150 to 200 nanometers for the spherical particles and 80 to 120 nanometers for the crumpled paper morphology particles.

EXAMPLE 4

Powder Surface Area Characterization

The BET isotherm method (Autosorb System, Quantachrome Instruments, Boynton Beach, Fla.) was used to determine the external surface areas of representative formulation i (spherical) and ii (crumpled paper morphology) powder samples. Samples were outgassed for 24 hours at ambient temperature before the isotherms were obtained via a 3 point method utilizing nitrogen gas as the adsorbate. Specific surface areas obtained via this method were 5.16 m2/gram for the formulation i and 8.10 $m^2$/gram for the formulation ii powder. AFM results supported the assumption that the BET isotherm method provided a measure of external particle surface area, with the surface areas as measured via AFM being equivalent to those obtained via the BET isotherm method (data not shown). To calculate the surface area factors (σ) for each formulation, the geometric diameters measured via RODOS at a dispersion pressure of 4 bar and the estimated particle densities were used to calculate the equivalent surface area of a solid (low density) particle via the following equation:

$$SA(\text{equivalent}) = \frac{4\pi R^2}{\frac{4}{3}\pi R^3 * p} = \frac{3}{R * p}$$

This procedure resulted in estimates of 5.00 $m^2$/gram for the formulation i and 5.24 $m^2$/gram for the formulation ii powders, which resulted in surface area factor (σ) estimates of 2.06 for the formulation i and 3.09 $m^2$/gram for the formulation ii powders. Using these results with equation 1 described above resulted in wall thickness estimates of approximately 160 nm for the formulation i and 100 nm for the formulation ii powders. These estimates correspond with the wall thicknesses estimated from the SEM images as described above. Thus, these results confirm the fact that, for powders with a given median geometric size and particle density, decreasing the wall thickness results in powders with increased surface areas and reduced cohesiveness.

EXAMPLE 5

Additional Examples of Drug-containing Crumpled Paper Morphology Powders.

Similar results can be obtained utilizing different excipients than those described above for both blank and drug-containing powders possessing crumpled paper morphologies. Utilizing spray drying methods similar to those described in Example 1 above, the following drug-containing powders possessing crumpled paper morphologies were formulated:

a. 68:20:10:2 DPPC:sodium citrate:calcium chloride:albuterol sulfate b. 58:20:20:2 DPPC:DPPE:lactose:estradiol.

The characterization results are displayed in Table 2.

TABLE 2

| | RODOS Size Measurements | | | | | | RODOS - IHA | | | | | BET |
|---|---|---|---|---|---|---|---|---|---|---|---|---|
| Powder | 0.25 bar | 0.5 bar | 1 bar | 2 bar | 4 bar | 0.25/2 ratio | 30 l/min | 60 l/min | 90 l/min | 30/90 ratio | Aerosizer MMAD | SA ($m^2$/gram) |
| a | 12.3 | 10.7 | 9.66 | 8.62 | 7.25 | 1.43 | 10.7 | 9.63 | 9.17 | 1.17 | 2.54 | 10.3 |
| b | 11.7 | 10.5 | 9.38 | 8.46 | 7.37 | 1.38 | 10.3 | 9.2 | 8.8 | 1.16 | 2.92 | 10.5 |

Estimated particle densities for powders a and b based on the VMGD measured at 4 bar and the MMAD measured via the Aerosizer are 0.12 g/$cm^3$ for Powder a and 0.16 g/$cm^3$ for Powder b (measured tap densities for Powders a and b were 0.12 and 0.11 g/$cm^3$, in agreement with the estimated particle densities). The procedure described in Example 4 above for determining the surface area factors of the powders resulted in estimates of 6.89 $m^2$/gram for Powder a and 5.09 $m^2$/gram for Powder b, which resulted in surface area factor (σ) estimates of 2.99 for Powder a and 4.13 for Powder b. AFM results again supported the assumption that the BET isotherm method provided a measure of external particle surface area, with the surface areas as measured via AFM being equivalent to those obtained via the BET isotherm method (data not shown). Using these results with equation 1 described above resulted in wall thickness estimates of approximately 80 nm for both Powders a and b.

EXAMPLE 6

A placebo powder, comprised of 70/20/10% by weight DPPC/Sodium Citrate/Calcium Chloride, that was used had the following characteristics: Dg=6.7um; =0.06 g/cm$^3$; Da=1.6um. The primary aerodynamic particle size characteristics were obtained using time-of-flight (AeroSizer/AeroDisperser) and the geometric particle size characteristics were obtained using laser diffraction (measured using the RODOS dry powder disperser and HELOS laser diffractometer, as described herein) operated at 1 and 2 bar. Emitted aerodynamic particle size characteristics were-obtained using Andersen cascade impaction (gravimetric analysis) operated at 28.3 L/min, for a total air volume of 2 L. Geometric particle size characteristics were obtained using laser diffraction (RODOS/HELOS, Sympatec, N.J.) with inhaler attachment operated at 60 L/min.

EXAMPLE 7

Highly dispersing powder can efficiently emit and penetrate into the lungs from a range of breath-activated dry powder inhalers (DPIs). A spray-dried powder was prepared comprised of sodium citrate, DPPC, calcium chloride buffer and a trace amount of a rhodamine fluorescent label. The powder possessed a median aerodynamic diameter of 2.1 μm (measured by the AeroDisperser and Aerosizer) and a geometric diameter of 11.0 μm (measured using the RODOS dry powder disperser and HELOS laser diffractometer, as described herein) and displayed excellent deaggregation properties.

5 milligrams of the powder were placed in the capsules using a semi-automated capsule filling device in the following inhalers: a breath-activated inhaler under development by Applicants (AIR Inhaler), the Spinhaler® (Fisons, Loughborough, U.K.), Rotahaler® (Glaxo-Wellcome, RTP, NC), FlowCaps® (Hovione, Loures, Portugal), Inhalator® (Boehringer-Ingelheim, Germany), and the Aerolizer® (Novartis, Switzerland). The Diskhaler (Glaxo-Wellcome, RTP, NC), was also tested for which 3 mg of the powder was machine-filled into the blister packs. Applicants connected each inhaler to a collapsed Andersen cascade impactor (consisting of stage 0 and the filter stage,) and extracted air at 60 L/minutes for 2 seconds after actuating the device. The fine particle fraction less than stage 0, having a 4.0 μm cut-off, was determined using fluorescent spectroscopy.

In this study, it was found that in each case, approximately 50% or more of the emitted dose displayed a median aerodynamic diameter (Da) less than 4 μm in size, indicating that the powder would efficiently enter the lungs of a human subject at a physiological breath rate, despite the simplicity of these breath-activated devices. It was also that large percentages of a nominal dose at low energy were emitted from not only single dose, breath-actuated inhalers but also from a range of breath-actuated dry powder inhalers (DPIs).

EXAMPLE 8

Nano-thin particles (i.e. hollow particles with wall thickness around 100 nm) were formed by spray drying ethanol/water cosolvent soltuions of drug and pharmaceutical excipients at inlet temperatures and drying rates that promoted the formation of a thin, dry shell that could collapse to varying degrees depending on the drying conditions. This process proved robust, permitting the formation of nano-thin particles with drugs including insulin, albeterol sulfate, estradiol, human growth hormone, and immunoglobulin, and excipients including lipids, sugars, and amino acids.

Two types of nano-thin particles were produced to test the hypothesis that thin-walled particles aerosolize more easily than thicker-walled particles of similar size and mass density. Powders A and B were designed of dextrin and dipalmitoyl phosphatidyl choline (DPPC) to contain particles possessing median geometric diameter of roughly 10 μm and tap density of approximately 0.08 g/cm$^3$. Powder A revealed a hollow sphere morphology and powder B a crumpled shell morphology. These morphological differences were related uniquely to the characteristic particle wall thickness h:

$$h \approx \frac{dp}{3\sigma p_s} \quad (1)$$

where $p_s$ is the skeletal mass density of the particle, and $\sigma$ the mean particle surface area per surface area of a nonporous sphere of equivalent spherical envelope diameter, d. Hence, according to the equation, particle wall thickness (h) dictates particle surface area ($\sigma$), or surface morphology, for hollow-particle powders of constant mass density (p) and size (d). $p_s$ was measured by pynonometry ($p_s$=1.2 g/cm$^3$) and $\sigma$ by atomic force microscopy (AFM) ($\sigma_A$=2.6; $\sigma_B$=5.0), leading to particle wall thickness estimates of h=200 nm for the spherical particle A and h=50 run for the crumpled particle B. These estimates were confirmed visually by transmission electron microscope (TEM) images, indirectly verifying the particle structure assumed as a result of the above equation.

Powders (A) and (B) were placed inside capsules of a Spinhaler® dry-powder inhaler (DPI) and actuated the inhaler into a multi-stage liquid impinger (MSLI) to evaluate the aerosolization efficiency of both powders. The MSLI simulates aerosol flight and deposition in the human lungs, with particles of an aerosol depositing on liquid-coated, parallel, stacked plates according to their aerodynamic size. Particles determined by the MSLI to possess aerodynamic size below about 5 μm, at a physiological flow rate (e.g. 60 L/min), are assumed sufficiently small to pass through the mouth and throat, and enter the lungs, during a human inhalation. The fraction of the original powder mass in the inhaler with aerodynamic size below 5 μm was termed the fine-particle fraction. This fraction was 40% for powder A, and 70% for powder B, using the MSLI with an inhalation flow rate of 60 L/min.

While this invention has been particularly shown and described with references to preferred embodiments thereof, it will be understood by those skilled in the art that various changes in form and details may be made therein without departing from the scope of the invention encompassed by the appended claims.

What is claimed is:

1. An improved particulate composition for delivery to the pulmonary system comprising spray-dried particles having a tap density of less than 0.4 g/cm$^3$ and a median geometric diameter greater than about 5 μm, and an external surface area greater than about 5 m$^2$/g.

2. The particles of claim 1 further comprising a drug.

3. The particles of claim 2 further comprising a pharmaceutical excipient.

4. The particles of claim 1 further comprising a ratio of median geometric diameters of between about 1.0 to about 1.5 as measured by laser diffraction (RODOS/HELOS system).

5. The particles of claim 4 having a skeletal density of at least about 1 g/cm$^3$.

6. The particles of claim 1 further comprising a ratio of median geometric diameter measurements taken using laser diffraction at a dispersion pressure of 0.25 bar and a dispersion pressure of 2.0 bar of between about 1.0 to about 1.5 as measured by laser diffraction.

7. A method for manufacturing a particulate composition for delivery to the pulmonary system comprising particles having a tap density of less than 0.4 g/cm$^3$ and a median geometric diameter greater than about 5 µm, and an external surface area greater than about 5 m$^2$/g comprising the steps of:
   a) preparing a solution comprising a therapeutically active agent;
   b) spray drying said solution under conditions which result in the formation of a thin walled spherical shell and wherein the spherical shell collapses.

8. The method of claim 7 wherein the solution comprises an ethanol:water mixture.

9. The method of claim 8 wherein the ratio of ethanol to water mixture is at least about 75% by volume.

10. The method of claim 8 wherein the ratio of ethanol to water mixture is at least about 85% by volume.

11. The method of claim 8 wherein the particles comprise a therapeutically active agent and a pharmaceutically acceptable excipient.

12. The method of claim 11 wherein the total amount of therapeutically active agent and a pharmaceutically acceptable excipient in the solution is less than about 4.0 g/l.

13. The method of claim 12 wherein the total amount of therapeutically active agent and a pharmaceutically acceptable excipient in the solution is less than about 1.0 g/l.

14. The method of claim 13 wherein the therapeutically active agent is a protein or peptide.

15. The method of claim 13 wherein the pharmaceutically acceptable excipient comprises dipalmitoylphosphatidyl choline.

16. The method of claim 8 wherein the inlet temperature of the spray dryer is less than about 100° C.

17. The method of claim 8 wherein the solution feed rate is less than about 52 ml/min.

* * * * *